(12) United States Patent
Papenfuss et al.

(10) Patent No.: US 10,271,830 B2
(45) Date of Patent: Apr. 30, 2019

(54) SURGICAL NAVIGATION INSTRUMENT (71) Applicant: LENKBAR, LLC, Naples, FL (US)

(72) Inventors: Erik H. Papenfuss, Naples, FL (US); Hans B. Papenfuss, Naples, FL (US)

(73) Assignee: Lenkbar, LLC, Naples, FL (US)

( * ) Notice: Subject to any disclaimer, the term of this patent is extended or adjusted under 35 U.S.C. 154(b) by 127 days.

(21) Appl. No.: 14/915,778

(22) PCT Filed: Sep. 8, 2014

(86) PCT No.: PCT/US2014/054520
§ 371 (c)(1),
(2) Date: Mar. 1, 2016

(87) PCT Pub. No.: WO2015/035291
PCT Pub. Date: Mar. 12, 2015

(65) Prior Publication Data
US 2016/0192915 A1    Jul. 7, 2016

Related U.S. Application Data (60) Provisional application No. 61/875,217, filed on Sep. 9, 2013.

(51) Int. Cl.
*A61B 17/00* (2006.01)
*A61B 17/16* (2006.01)
*A61B 34/20* (2016.01)

(52) U.S. Cl.
CPC .... *A61B 17/00234* (2013.01); *A61B 17/1633* (2013.01); *A61B 17/1631* (2013.01);
(Continued)

(58) Field of Classification Search
CPC .. A61B 2017/00314; A61B 2017/2906; A61B 2017/2908; A61B 17/00234;
(Continued)

(56) References Cited

U.S. PATENT DOCUMENTS

| 5,383,852 A | 1/1995 | Stevens-Wright |
| 5,632,433 A | 5/1997 | Grant |

(Continued)

OTHER PUBLICATIONS

International Preliminary Report on Patentability and Written Opinion of the International Searching Authority for International Application No. PCT/US2014/054520 dated Mar. 15, 2016.
(Continued)

*Primary Examiner* — Todd J Scherbel
*Assistant Examiner* — Brooke Nicole Labranche
(74) *Attorney, Agent, or Firm* — RatnerPrestia (57) ABSTRACT

An instrument for navigating a surgical device includes a hollow shaft having a longitudinal axis and a distal end. The distal end of the hollow shaft includes a flexible section, a handle and an articulation surface positioned adjacent the handle. The handle is polyaxially displaceable against the articulation surface and relative to the longitudinal axis of the hollow shaft. At least one tensioning element extends substantially parallel to the longitudinal axis of the hollow shaft. The at least one tensioning element is operable to bend the flexible section in response to polyaxial displacement of the handle relative to the longitudinal axis of the hollow shaft.

22 Claims, 4 Drawing Sheets

(52) U.S. Cl.
CPC .............. *A61B 2017/00314* (2013.01); *A61B 2017/00327* (2013.01); *A61B 2034/2055* (2016.02)

(58) Field of Classification Search
CPC ............ A61B 17/1631; A61B 17/1633; A61B 2017/00327; A61B 2034/2055
See application file for complete search history.

(56) References Cited

U.S. PATENT DOCUMENTS

| | | | | |
|---|---|---|---|---|
| 8,100,824 | B2* | 1/2012 | Hegeman | ............. A61B 1/0055 600/139 |
| 8,366,559 | B2* | 2/2013 | Papenfuss | .......... A61B 17/1631 464/149 |
| 2007/0221700 | A1* | 9/2007 | Ortiz | ..................... A61B 34/72 227/175.1 |
| 2009/0171147 | A1 | 7/2009 | Lee et al. | |
| 2011/0184459 | A1* | 7/2011 | Malkowski | ............ A61B 17/29 606/206 |
| 2012/0053641 | A1 | 3/2012 | Meridew | |

OTHER PUBLICATIONS

Supplementary European Search Report for Application No. 14842114.2, dated Mar. 21, 2017, 7 pages.
International Search Report for International Application No. PCT/US2014/054520 dated Dec. 31, 2014.
Written Opinion of the International Searching Authority for International Application No. PCT/US2014/054520 dated Dec. 31, 2014.
Australian Examination Report for Australian Application No. 2014317934, dated Jun. 25, 2018, 3 pages.

* cited by examiner

SURGICAL NAVIGATION INSTRUMENT

RELATED APPLICATIONS

This application is the U.S. National Phase entry of International Application No. PCT/US2014/054520, filed Sep. 8, 2014, which claims the benefit of priority of U.S. Provisional Application Ser. No. 61/875,217, filed Sep. 9, 2013. The contents of International Application No. PCT/US2014/054520 and U.S. Provisional Application Ser. No. 61/875,217 are incorporated by reference herein in their entireties.

FIELD

The present disclosure relates generally to surgical instrumentation, and more specifically to a steerable navigation instrument for use in various surgical procedures.

BACKGROUND

Conventional surgical instruments with rigid shafts are not well suited for surgical procedures because they have limited maneuverability and range of motion. Therefore, surgical instruments with flexible shafts have been developed to provide a desired level of maneuverability during navigation of the instrument. For example, instruments have been developed with flexible shafts that drill into bone, ream bone, punch holes into bone, tap anchors or screws into bone, advance anchors or screws into bone, and secure sutures to bone and tendons.

Not all instruments with flexible shafts have a control mechanism that allows surgeons to easily maneuver the shafts with precision, and/or maneuver the shafts through a complete 360° range of motion. In addition, not all instruments with flexible shafts having a locking mechanism that allows a surgeon to find a desired curvature or angle for the flexible shaft, and easily lock that curvature or angle in position. Therefore, control mechanisms for existing instruments with flexible surgical shafts are in need of improvement.

SUMMARY

Drawbacks of conventional surgical instruments having flexible shafts are resolved in many respects by surgical navigation instruments in accordance with the invention.

In one aspect, an instrument for navigating a surgical device includes a hollow shaft having a longitudinal axis and a distal end. The distal end of the hollow shaft includes a flexible section.

In another aspect, the foregoing instrument includes a handle and an articulation surface positioned adjacent the handle. The handle is polyaxially displaceable against the articulation surface and relative to the longitudinal axis of the hollow shaft.

In another aspect, at least one tensioning element extends substantially parallel to the longitudinal axis of the hollow shaft. The at least one tensioning element is operable to bend the flexible section in response to polyaxial displacement of the handle relative to the longitudinal axis of the hollow shaft.

In another aspect, the handle includes at least one disc extending in a plane that is substantially perpendicular to the longitudinal axis of the hollow shaft.

In another aspect, the articulation surface includes a rounded bearing surface.

In another aspect, the articulation surface includes a spherical shaped surface.

In another aspect, the articulation surface includes a sphere.

In another aspect, the at least one tensioning element includes a first pair of cables that are diametrically opposed to one another relative to a diameter of the hollow shaft.

In another aspect, the at least one tensioning element further comprises a second pair of cables that are diametrically opposed to one another relative to the diameter of the hollow shaft. The first and second pairs of cables are radially offset 90 degrees from one another relative to the diameter of the hollow shaft.

In another aspect, the at least one tensioning element extends inside the hollow shaft.

In another aspect, the flexible section includes a first interlocking section and a second interlocking section.

In another aspect, each of the first interlocking section and second interlocking section has at least one pin and at least one socket.

In another aspect, the at least one pin is substantially triangular shaped, and the at least one socket is substantially triangular shaped.

In another aspect, the at least one pin on the first interlocking section has a circumferential width that increases as the at least one pin on the first interlocking section extends from the outer surface of the shaft to the inner surface of the shaft, so that the at least one pin on the first interlocking section becomes gradually wider toward the inner surface.

In another aspect, the at least one pin on the second interlocking section has a circumferential width that decreases as the at least one pin on the second interlocking section extends from the outer surface of the shaft to the inner surface of the shaft, so that the at least one pin on the second interlocking section becomes gradually narrower toward the inner surface.

In another aspect, the first and second interlocking sections are cut at opposing angles to create at least one inward angled surface and at least one outward angled surface, the at least one inward angled surface being adjacent to the at least one outward angled surface.

In another aspect, the handle is pivotable on the articulation surface to apply variable amounts of tension to the at least one tensioning element to bend the flexible section.

BRIEF DESCRIPTION OF THE DRAWINGS

The foregoing summary and the following detailed description will be better understood in conjunction with the examples illustrated in the accompanying drawing figures, of which.

DETAILED DESCRIPTION

Surgical navigation instruments in accordance with the invention are designed to guide flexible instruments to treatment areas that require the instruments to be maneuvered through non-linear pathways and bends. In one embodiment, the navigation instrument is cannulated, with a passage that extends through the entire length of the instrument. The passage allows smaller flexible instruments to be directed through the navigation instrument to a treatment area in the patient. The flexible section of the navigation instrument can be used to provide a pathway for navigating multiple devices around extreme bends, where a straight approach is not possible or practical. In preferred embodiments, the flexible section of the navigation instrument is configured to be flexed around one or more bends to a desired configuration, at which point the flexible section can be locked in that configuration. This locking feature allows the flexible section of the navigation instrument to be maneuvered along a tortuous pathway, through one or more bends, and then be locked in that configuration to provide a fixed pathway that can be used repeatedly to guide different instruments to the same treatment location. By fixing the pathway, the navigation instrument allows a surgeon to guide a series of different instruments through the navigation instrument to the treatment site. This avoids having to independently navigate each instrument or device through a tortuous path to the treatment location.

By way of example, a surgeon can initially insert camera device though a surgical navigation instrument in accordance with the invention, with the camera positioned at the distal end of the flexible section. The surgical navigation instrument and camera can then be inserted into a patient. Using the camera and a video monitor, the surgeon can navigate the distal end of the flexible section through one or more bends, and around one or more obstructions, until the distal end is positioned at the proposed treatment site. Once the distal end reaches the proposed treatment site, the surgeon can use a locking mechanism to lock the curvature of the flexible shaft. Once the flexible shaft is locked, the surgeon can withdraw the camera from the navigation instrument and insert another flexible instrument, such as a flexible drill shaft, through the navigation instrument so that the drill shaft is directed to the treatment site where the camera was previously positioned. The drill can then be operated through the navigation instrument to drill a small hole in bone, for example. After the hole is drilled, the drill can be withdrawn from the navigation instrument, and another flexible instrument, such as a surgical screwdriver having a flexible shaft loaded with a screw and suture, can be inserted through the navigation instrument and directed to the treatment site where the drill was previously positioned. The steps for withdrawing instruments and inserting different instruments can be repeated over and over, with each new instrument being automatically guided and directed to the treatment site by the locked navigation instrument. This avoids having to repeat the task of navigating each instrument around the obstruction(s) to the treatment site.

In one embodiment, an instrument for navigating a surgical device is provided. The instrument includes a hollow shaft having a longitudinal axis and a distal end, the distal end of the hollow shaft comprising a flexible section. The instrument also includes a handle, and an articulation surface positioned adjacent the handle, with the handle being polyaxially displaceable against the articulation surface and relative to the longitudinal axis of the hollow shaft. One or more tensioning elements extend substantially parallel to the longitudinal axis of the hollow shaft. The one or more tensioning elements may be in the form of wires, cables, bands or other suitable structures for transferring tensile force. The one or more tensioning elements is/are operable to bend the flexible section in response to polyaxial displacement of the handle.

The handle may be pivotable on the articulation surface to apply variable amounts of tension to the one or more tensioning elements, and bend the flexible section in different directions. Various configurations may be utilized for the handle. For example, the handle can include at least one disc extending in a plane that is substantially perpendicular to the longitudinal axis of the hollow shaft. The handle can also be in the form of a knob, a lever, or a cylindrical shaft having a ball or pad on a proximal end of the shaft, similar to a joystick.

The articulation surface may be a rounded bearing surface, including but not limited to an elliptical-shaped surface or a spherical-shaped surface. Where the articulation surface is spherical-shaped, the articulation surface may be in the form of a sphere that forms a ball joint.

The plurality of tensioning elements can be arranged uniformly around the diameter of the hollow shaft. That is, each tensioning element can be angularly offset from adjacent tensioning elements with respect to the longitudinal axis by a constant angle. For example, the plurality of tensioning elements can include a first pair of cables that are diametrically opposed to one another relative to a diameter of the hollow shaft. The plurality of tensioning elements can further include a second pair of cables that are diametrically opposed to one another relative to the diameter of the hollow shaft. The four cables can be radially offset from one another by an angle of 90 degrees relative to the diameter of the hollow shaft. Each of the cables can extend inside the hollow shaft. This arrangement can also be used with wires, bands and other types of tensioning elements.

The flexible section may include a first interlocking section and a second interlocking section. Each of the first interlocking section and second interlocking section may include at least one pin and at least one socket. The pin may be substantially triangular shaped, and the socket may be substantially triangular shaped. The pin on the first interlocking section may have a circumferential width that increases as the pin extends from the outer surface of the shaft to the inner surface of the shaft, so that the pin becomes gradually wider toward the inner surface.

The pin on the second interlocking section may have a circumferential width that decreases as the pin extends from the outer surface of the shaft to the inner surface of the shaft, so that the pin becomes gradually narrower toward the inner surface.

The first and second interlocking sections may be cut at opposing angles to create at least one inward angled surface and at least one outward angled surface, the at least one inward angled surface being adjacent to the at least one outward angled surface.

Figure 1:
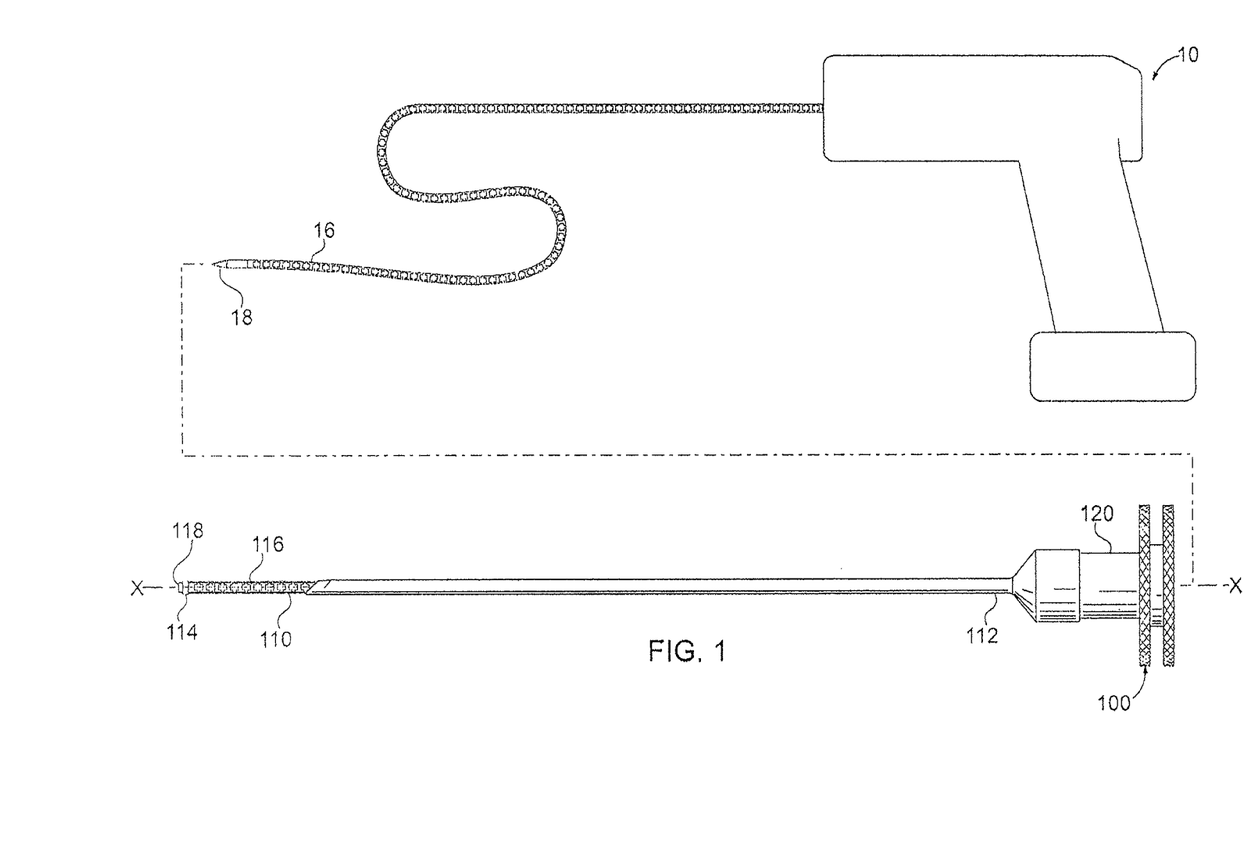
FIG. 1 is a side view of a surgical navigation instrument in accordance with one exemplary embodiment of the invention, the surgical navigation instrument being shown in a first operative state, with a surgical drill in accordance with the invention.
Figure 2:
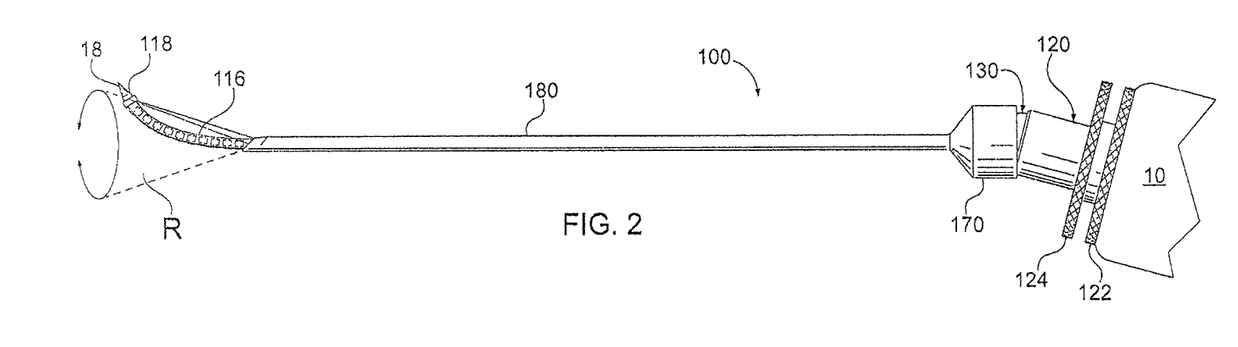
FIG. 2 is a side view of the surgical navigation instrument in FIG. 1, with the surgical navigation instrument being shown in a second operative state, and with the surgical drill inserted through the navigation instrument.

Referring now to FIGS. 1 and 2, a surgical navigation instrument 100 in accordance with an example of the invention will be described in more detail. Instrument 100 includes a hollow shaft 110 having a proximal end 112, a distal end 114, and a longitudinal axis "X" extending through the proximal and distal ends. Distal end 114 of hollow shaft 110 includes a flexible section 116. Hollow shaft 110 is cannulated with a longitudinal passage 118 extending between proximal end 112 and distal end 114. Passage 118 is adapted to receive the shafts of various instruments, including but not limited to surgical drills, drivers and other instruments. FIG. 1 schematically shows a surgical drill 10 with a flexible shaft 16 and drill bit 18. Flexible shaft 16 has an outer diameter that is less than the inner diameter of passage 118. Passage 118 is adapted to receive flexible shaft 16 and guide the flexible shaft to direct drill bit 18 to the distal end of flexible section 116.

Figures 3, 5:
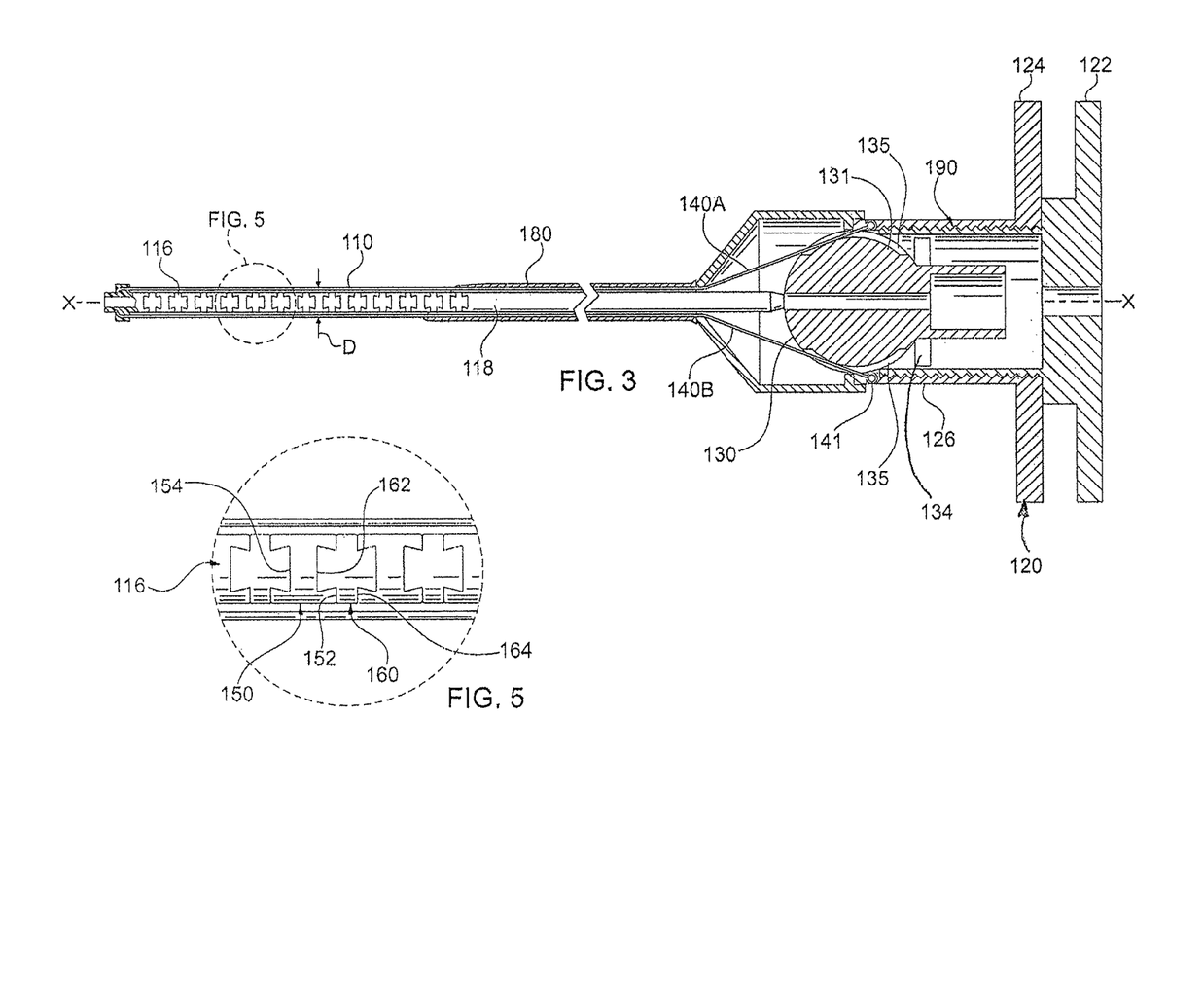
FIG. 3 is an enlarged side cross-section view of the surgical navigation instrument in FIG. 1, with a section truncated for clarity.
FIG. 5 is an enlarged view of a section of the surgical navigation instrument in FIG. 3.

Articulation elements in accordance with the invention can be integrated with the instrument in a number of arrangements, which may or may not include attachment of the articulation element with the hollow shaft and other components. Referring to FIGS. 2 and 3, navigation instrument 100 includes a handle 120 and an articulation element 130. Articulation element 130 is in the form of a ball 131 having a bearing surface 136. Ball 131 connects with proximal end 112 of hollow shaft 110. In other embodiments, the ball need not connect with the hollow shaft, but may engage with the hollow shaft in the assembled state.

Handle 120 includes an outer disc 122 and an inner disc 124 extending in a plane that is generally parallel to the plane of the inner disc, and substantially perpendicular to the longitudinal axis X of hollow shaft 110. Handle 120 is polyaxially displaceable against articulation element 130, relative to longitudinal axis X of hollow shaft 110. That is, handle 120 is pivotable as it slides along the rounded bearing surface 136 of ball 131. In this configuration, articulation element 130 acts as a ball joint or universal joint.

One or more tensioning elements extend from handle 120 to distal end 114 of hollow shaft 110. The tensioning elements may be in the form of wires, cables, bands or other suitable structures for transferring tensile forces between handle 120 and distal end 114, as noted above. For example, instrument 100 has a plurality of tensioning elements in the form of four cables 140A, 140B, 140C and 140D. Cables 140A-140D converge toward one another as they extend from ball 131 toward distal end 114 of hollow shaft 110. After a certain point, cables 140A-140D extend substantially parallel to longitudinal axis X of hollow shaft 110.

Cables 140A-140D are operable to bend flexible section 116 in response to polyaxial displacement of handle 120. Handle 120 is pivotable on articulation element 130 to apply variable amounts of tension to each of the cables. The different amounts of tension applied to cables 140A-140D exert different forces on distal end 114 of hollow shaft 110, causing flexible section 116 to bend in different directions. When handle 120 is pivoted relative to ball 131, flexible section 116 can pivot polyaxially and seamlessly bend through a range of 360° relative to longitudinal axis X of hollow shaft 110. The pivot range allows flexible section 116 to move within a cone-shaped range R, as shown in FIG. 2.

Figure 4:
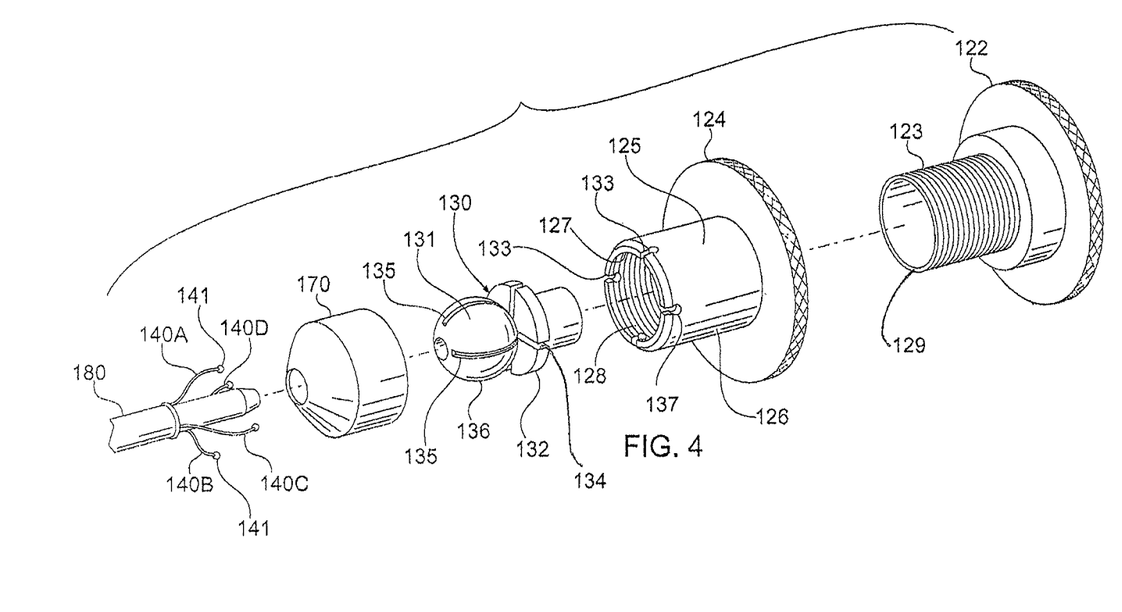
FIG. 4 is an exploded perspective view of the surgical navigation instrument in FIG. 1, with a section truncated for clarity.

Referring to FIGS. 3 and 4, inner disc 124 of handle 120 connects to a tubular socket 126. Socket 126 includes a socket wall 127 that surrounds an interior socket space 128. Socket space 128 is adapted to receive a portion of articulation element 130. Articulation element 130 includes a flange 132 adjacent ball 131. Flange 132 has four slots 134 uniformly arranged around the circumference of the flange. Ball 131 also includes slots 135 that are axially aligned with slots 134 as shown. Each aligned pair of slots 134 and 135 receives one of the cables 140A-140D. Each of cables 140A-140D has a hub 141 attached to an end of the cable. As will be explained in more detail, each hub 141 secures its respective cable inside handle 120.

Instruments in accordance with the invention can feature tensioning elements that are exposed on the exterior of the articulation element. Alternatively, instruments in accordance with the invention may include a housing that covers the articulation element and tensioning elements. For example, instrument 100 includes a housing 170 that covers the ball 131 and cables 140A-140D. Instruments in accordance with the invention may also feature an outer sleeve, such as sleeve 180, that surrounds a portion of hollow shaft 110 to cover cables 140A-140D.

Instruments in accordance with the invention can also feature a variety of cable configurations that interconnect the handle to the flexible section. In instrument 100, the first pair of cables 140A and 140B are diametrically opposed to one another relative to a diameter "D" of hollow shaft 110. Similarly, cables 140C and 140D are diametrically opposed to one another relative to diameter D of hollow shaft 110. Cables 140A-140D are radially offset 90 degrees from one another relative to the diameter D, so that the cables are spaced apart equally, in a uniform arrangement around the diameter of hollow shaft 110.

Instruments in accordance with the invention may include one or more flexible shaft arrangements. One possible flexible shaft arrangement is described in U.S. Pat. No. 8,366,559, issued to Applicant on Feb. 5, 2013, the contents of which is incorporated by reference herein in its entirety and for all purposes. Referring to FIG. 5, for example, flexible section 116 includes a first interlocking section 150 and a second interlocking section 160. First interlocking section 150 has at least one pin 152 and at least one socket 154. Likewise, second interlocking section 160 has at least one pin 162 and at least one socket 164. Each pin is substantially triangular or trapezoidal shaped, and each socket is substantially triangular or trapezoidal shaped, having the same general shape as the pin.

Pin 152 on first interlocking section 150 has a circumferential width that increases as the pin extends radially inwardly from the outer surface of the flexible section, so that the pin becomes gradually wider toward the interior of the flexible section. Pin 162 on second interlocking section 160 has a circumferential width that decreases as the pin extends radially inwardly from the outer surface of the flexible section, so that the pin becomes gradually narrower toward the interior of the flexible section. The first and second interlocking sections 150 and 160 are cut at opposing angles to create at least one inward angled surface and at least one outward angled surface, the inward angled surface being adjacent to the outward angled surface.

Navigation instruments in accordance with the invention preferably include a locking mechanism to lock the flexible section once it has been flexed to a desired configuration to access a proposed treatment site. Referring to FIGS. 3 and 4, for example, a locking mechanism 190 is provided by a threaded engagement between an inner sleeve 123 and an outer sleeve 125 inside handle 120. Inner sleeve 123 is attached to outer disc 122, and outer sleeve 125 is attached to inner disc 124. Outer disc 122 and inner sleeve 123 are rotatable relative to inner sleeve 123 to axially advance the inner sleeve between an unlocked position and a locked position. In the unlocked position, inner sleeve 123 does not engage articulation element 130, allowing the handle to be pivoted to bend flexible section 116. In the locked position, inner sleeve 123 bears against articulation element 130, locking the flexible section 116 in a fixed configuration.

Flexible sections of navigation instruments in accordance with the invention can be locked in several ways. For example, flexible section 116 can be locked in a fixed configuration by rotating outer disc 122 and inner sleeve 123 clockwise (or counterclockwise depending on thread direction) relative to outer sleeve 125 to advance the inner sleeve distally relative to the outer sleeve. Outer disc 122 and inner sleeve 123 are rotated until a distal end 129 of the inner sleeve bears against articulation element 130. As inner sleeve 123 bears against articulation element 130, ball 131 is compressed between the inner sleeve and housing 170. This compression force locks the position of outer disc 122, inner disc 124 and ball 131 relative to housing 170, preventing further articulation, and locking the curvature of flexible section 116.

Outer sleeve 125 has a plurality of slots 133 incrementally spaced around the circumference of the sleeve. Each slot 133 has a widened section 137 that receives and retains a hub 141 associated with one of the cables 140A-140D. When outer disc 122 is in the unlocked position, the outer disc and inner disc 124 can be pivoted relative to ball 131 to apply different amounts of tension to cables 140A-140D to bend flexible section 116 in desired directions.

While preferred embodiments of the invention have been shown and described herein with reference to specific embodiments, the invention is not intended to be limited to the details shown. The embodiments described herein are provided by way of example only. Numerous variations, changes and substitutions will occur to those skilled in the art without departing from the scope of the invention. Accordingly, it is intended that the appended claims cover all such variations as fall within the scope of the invention.

What is claimed:

1. An instrument for navigating a surgical device, the instrument defining a proximal end and comprising: a hollow shaft having a longitudinal axis, at least a portion of the hollow shaft comprising a flexible section; a handle at the proximal end of the instrument, the handle comprising a first handle portion and a second handle portion; an articulation surface positioned distally with respect to the first handle portion and the second handle portion, and positioned proximally with respect to the flexible section, the handle being polyaxially displaceable relative to the articulation surface and relative to the longitudinal axis of the hollow shaft; at least one tensioning element in operable communication with the handle and the flexible section to bend the flexible section in response to polyaxial displacement of the handle relative to the longitudinal axis of the hollow shaft; an outer sleeve extending from the first handle portion; and an inner sleeve extending from the second handle portion and into the outer sleeve, the inner sleeve axially displaceable relative to the outer sleeve between a distal locked position, in which the inner sleeve bears against the articulation surface to lock the flexible section in a fixed configuration, and a proximal unlocked position, in which the inner sleeve does not engage the articulation surface to allow the flexible section to bend in response to polyaxial displacement of the handle relative to the longitudinal axis of the hollow shaft.

2. The instrument of claim 1, wherein the handle comprises at least one disc extending in a plane that is substantially perpendicular to the longitudinal axis of the hollow shaft.

3. The instrument of claim 1, wherein the articulation surface comprises a rounded bearing surface.

4. The instrument of claim 1, wherein the articulation surface comprises a spherical shaped surface.

5. The instrument of claim 1, wherein the articulation surface comprises a sphere.

6. The instrument of claim 1, wherein the at least one tensioning element comprises a first pair of cables that are diametrically opposed to one another relative to a diameter of the hollow shaft.

7. The instrument of claim 6, wherein the at least one tensioning element further comprises a second pair of cables that are diametrically opposed to one another relative to said diameter of the hollow shaft.

8. The instrument of claim 7, wherein the first and second pairs of cables are radially offset 90 degrees from one another relative to the diameter of the hollow shaft.

9. The instrument of claim 1, wherein the at least one tensioning element extends inside the hollow shaft.

10. The instrument of claim 1, wherein the flexible section comprises a first interlocking section and a second interlocking section.

11. The instrument of claim 10, wherein each of the first interlocking section and second interlocking section has at least one pin and at least one socket.

12. The instrument of claim 11, wherein each pin is substantially triangular shaped, and each socket is substantially triangular shaped.

13. The instrument of claim 11, wherein the at least one pin on the first interlocking section has a circumferential width that increases as said at least one pin on the first interlocking section extends from an outer surface of the shaft to an inner surface of the shaft, so that said at least one pin on the first interlocking section becomes gradually wider toward the inner surface.

14. The instrument of claim 11, wherein the at least one pin on the second interlocking section has a circumferential width that decreases as said at least one pin on the second interlocking section extends from an outer surface of the shaft to an inner surface of the shaft, so that said at least one pin on the second interlocking section becomes gradually narrower toward the inner surface.

15. The instrument of claim 10, wherein the first and second interlocking sections are cut at opposing angles to create at least one inward angled surface and at least one outward angled surface, said at least one inward angled surface being adjacent to the at least one outward angled surface.

16. The instrument of claim 1, wherein the handle is pivotable on the articulation surface to apply variable amounts of tension to the at least one tensioning element to bend the flexible section.

17. The instrument of claim 1, wherein the instrument defines a longitudinal passage through the hollow shaft, the articulation surface and the handle, the longitudinal passage adapted to receive a surgical instrument shaft into the handle and direct said surgical instrument shaft to a distal end of the flexible section.

18. The instrument of claim 1, wherein the outer sleeve and the inner sleeve are connected by a threaded engagement, and the first handle portion is rotatable relative to the second handle portion to axially displace the inner sleeve relative to the outer sleeve between the locked and unlocked positions.

19. The instrument of claim 18, wherein the first handle portion is rotatable relative to the second handle portion about the longitudinal axis of the hollow shaft to axially displace the inner sleeve relative to the outer sleeve.

20. The instrument of claim 1, wherein the at least one tensioning element is coupled to the outer sleeve to connect the handle in operable communication with the flexible section.

21. The instrument of claim 1, wherein in the distal locked position, the inner sleeve does not engage the at least one tensioning element.

22. The instrument of claim 1, wherein the outer sleeve is integrally attached to the first handle portion, and the inner sleeve is integrally attached to the second handle portion.

* * * * *